United States Patent [19]

Hiraga et al.

[11] 4,157,256

[45] Jun. 5, 1979

[54] TETRAHYDROPHTHALIMIDE AND HERBICIDE CONTAINING THE SAME

[75] Inventors: Kunikazu Hiraga, Izumi; Shoichi Shibayama, Takatsuki; Isao Yanai, Osaka; Tatsuo Harada, Kawachinagano, all of Japan

[73] Assignee: Nihon Nohyaku Co. Ltd., Tokyo, Japan

[21] Appl. No.: 872,339

[22] Filed: Jan. 25, 1978

[30] Foreign Application Priority Data

Jan. 28, 1977 [JP] Japan ................................. 52-8334

[51] Int. Cl.$^2$ .................... C07D 209/48; A01N 9/22; A01N 9/24; A01N 9/12
[52] U.S. Cl. ................................. 71/95; 260/326 H; 260/326 A

[58] Field of Search .......... 260/326 S, 326 H, 326 A; 71/95

[56] References Cited

U.S. PATENT DOCUMENTS

| 3,878,224 | 4/1975 | Matsui | 260/326 S |
| 3,984,435 | 10/1976 | Matsui | 260/326 A |

OTHER PUBLICATIONS

Yugupol'ski et al, Chem. Abs. 70, 96324c (1969).

*Primary Examiner*—Mark L. Berch
*Attorney, Agent, or Firm*—Cushman, Darby & Cushman

[57] ABSTRACT

N-(p-trifluoromethoxyphenyl)-3,4,5,6-tetrahydrophthalimide and N-(p-trifluoromethylthiophenyl)-3,4,5,6-tetrahydrophthalimide are capable of controlling annual and perennial weeds with high selectivity.

4 Claims, No Drawings

TETRAHYDROPHTHALIMIDE AND HERBICIDE CONTAINING THE SAME

This invention relates to 3,4,5,6-tetrahydrophthalimide derivatives represented by the general formula (I),

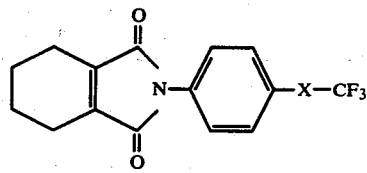

wherein X represents an oxygen atom or a sulfur atom. It relates also to a process for producing said derivatives and the usage of said derivatives.

The compounds represented by the general formula (I) are useful especially as herbicides (including algicides; the same applies hereinafter).

The compound represented by the general formula (I) is a novel compound not reported in the literature. It is readily synthesized, for example, by way of a synthetic route shown schematically below,

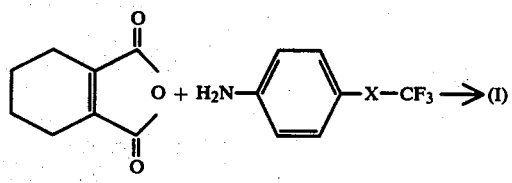

wherein X is the same as defined above. Thus, the intended compound can be readily synthesized in a high yield by reacting 3,4,5,6-tetrahydrophthalic anhydride with p-trifluoromethoxyaniline or p-trifluoromethylthioaniline in a suitable solvent. For the solvent, an organic acid such as, for example, acetic acid or propionic acid may be used. The reaction is carried out advantageously with heating under reflux. After completion of the reaction, the intended reaction product is separated in a customary way and, if necessary, further purified.

The group of the compounds represented by the general formula (I) consists of the following members:

(1) N-(p-trifluoromethoxyphenyl)-3,4,5,6-tetrahydrophthalimide, melting point 117°-118.5° C.
(2) N-(p-trifluoromethylthiophenyl)-3,4,5,6-tetrahydrophthalimide, melting point 112°-114° C.

These 3,4,5,6-tetrahydrophthalimide derivatives are capable of controlling annual and perennial weeds grown in paddy field, upland field, orchard and swamp, such as barnyard grass (*Echinochloa Crusgalli* L., an annual gramineous grass which is a typical weed grown in paddy field and strongly injurious), monochoria (*Monochoria vaginalis* Presl, a strongly injurious annual weed of Pontederiaceae family grown in paddy field), umbrella plant (*Cyperus difformis* L., an injurious annual cyperaceous weed grown in paddy field), slender spikerush (*Eleocharis acicularis* Roem. et Schult, a typical injurious perennial weed of a paddy field, grown also in swamp and waterway), Arrowhead (*Sagittaria pygmaea* Miq., an injurious perennial weed of Alismataceae family, grown in paddy field, swamp and ditch), Hotarui (*Scirpus juncoides* Roxb. var. hotarui ohwi., a perennial cyperaceous weed grown in paddy field, swamp and ditch), large crabgrass (*Digitaria adscendeus* Henr., an annual gramineous grass which is a typical strongly injurious weed grown in upland field and orchard), and Redroot pigweed (*Amaranthus varidis* L., an annual weed of Amaranthus family grown in vacant land, roadside and upland field).

One of the current trends in paddy rice cultivation is a rapid spread of mechanical transplanting of young rice seedlings having low chemical resistance. Consequently, development of an early stage herbicide having a selectivity higher than those of conventional herbicides is strongly demanded. Because of their highly selective herbicidal activities, the compounds represented by the general formula (I) will certainly become most valuable herbicides in paddy rice cultivation by use of the above-said technique of young seedling transplantation and a technique of direct sowing of paddy rice on well-drained paddy field, both techniques requiring a highly selective herbicide.

Since the compounds of the general formula (I) exhibit an excellent controlling action against weeds in the initial stage of emergence, their characteristic physiological activities can be manifested more effectively by treating with the compounds the areas in which useful plants are to be grown or the areas in which useful plants have already been planted (including such areas as orchard where the useful plants have been set out) but weeds have not yet emerged or by treating the areas in which useful plants have been sown but not yet emerged. However, the modes of the use of the present herbicide are not limited to those described above. It can also be used as a middle stage herbicide in paddy fields and, further, as a herbicide for controlling such general weeds as those usually grown on, for examples, reaped fields, temporarily non-cultivated paddy fields and upland fields, ridges between paddy fields, agricultural pathways, waterways, prepared land intended for use as pasture, graveyards, parks, roads, playgrounds, unoccupied areas of the building sites, reclaimed lands, railways, and forests. Herbicidal treatment of such areas is carried out preferably (and also economically) but not necessarily prior to the emergence of weeds.

In applying the present compound as a herbicide, it is employed generally in a form which is convenient to use and prepared by following the customary pesticide formulating procedures. Thus, the present compounds may be blended with suitable carriers and, if necessary, auxiliary agents to effect dissolution, dispersion, mechanical mixing, impregnation, adsorption, or adhesion, resulting in dispersions, emulsifiable concentrates, solutions, wettable powders, dusts, granules, tablets, etc.

The inert carriers to be used in the formulations may be either solids or liquids. Examples of the materials which can be used as solid carriers include vegetable powders such as soybean flour, cereal flour, wood flour, bark flour, saw dust, powdered tabaco stalk, powdered walnut shell, bran, powdered cellulose, and extraction residues of vegetables; cellulosic materials such as paper, corrugated fiberboard and waste cloth; synthetic polymers such as powdered synthetic resins; inorganic or mineral products such as clays (for example, kaolin, bentonite and acid clay), talcs (for example, talc and pyrophillite), siliceous substances [for example, diatomaceous earth, siliceous sand, mica, and "white carbon" (commercial highly dispersed synthetic silicic acid, also called hydrated finely divided silica or hydrated silicic acid; some commercial products contain calcium silicate as major ingredient)], activated carbon, powdered sulfur, pumice, calcined diatomaceous earth, ground brick, fly ash, sand, calcium carbonate and calcium phosphate; chemical fertilizers such as ammonium sulfate, ammonium phosphate, ammonium nitrate, urea and ammonium chloride; and farmyard manure. These materials are used each alone or as mixtures of two or more of these.

The materials usable as liquid carriers are selected from those which are solvents for the active compounds and those which are non-solvents but can disperse the active compounds by the aid of auxiliary agents. Examples of liquid carriers which are used each alone or in combinations of two or more are as follows: water, alcohols (for example, methanol, ethanol, isopropanol, butanol and ethylene glycol), ketones (for example, acetone, methyl ethyl ketone, methyl isobutyl ketone, diiisobutyl ketone and cyclohexanone), ethers (for example, ethyl ether, dioxane, Cellosolves, dipropyl ether and tetrahydrofuran), aliphatic hydrocarbons (for example, gasoline and mineral oils), aromatic hydrocarbons (for example, benzene, toluene, xylene, solvent naphtha and alkylnaphthalenes), halohydrocarbons (for example, dichloroethane, chlorinated benzenes, chloroform and carbon tetrachloride), esters (for example, ethyl acetate, dibutyl phthalate, diisopropyl phthalate and dioctyl phthalate), acid amides (for example, dimethylformamide, diethylformamide and dimethylacetamide), nitriles (for example, acetonitrile) and dimethyl sulfoxide.

The auxiliary agents which are used are as shown below. These substances are used in accordance with the purpose. In some cases, combinations of two or more auxiliary agents are used. In some other cases, no auxiliary agent is used at all.

For the purpose of emulsification, dispersion, solubilization or wetting of the active compounds, surface active agents are used. Examples of such agents are polyoxyethylene alkylaryl ethers, polyoxyethylene alkyl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

For the purpose of stabilization of dispersions, tackification or agglomeration of the active compounds, it is possible to use, for example, casein, gelatin, starch, alginic acid, methylcellulose, carboxymethylcellulose, gum arabic, polyvinyl alcohol, turpentine oil, rice bran oil, bentonite and ligninsulfonates.

For the purpose of improving the flow property of solid compositions, it is recommendable to use waxes, stearates and alkyl phosphates.

As peptizers for a dispersible composition, it is also recommendable to use naphthalenesulfonic acid condensation products and polyphosphates.

It is also possible to add a defoamer such as, for example, a silicone oil.

For destroying various weeds or inhibiting their growth or protecting useful plants from the injury due to weeds, a weed destroying dosage or a weed growth inhibiting dosage of the present herbicidal composition is applied as such or after suitable dilution with water and the like or in the form of dispersion to the soil or the foliage of weeds in the area where the emergence or growth of weeds is undesirable.

The amount to be used of the present herbicide depends on various factors such as, for example, purpose of application, weeds to be controlled, state of emergence or growth of weeds or crops, tendency of the emergence of weeds, weather, environmental conditions, type of the herbicide composition, mode of application, type of the field to be applied, and time of application.

In applying the present herbicidal composition alone as a selective herbicide, it is suitable to select the dosage of the present active compound from the range of 90 to 250 g per 10 ares. When it is used in combination with other herbicides, it is possible to select the dosage from the range of smaller rates of application by taking into account the increased efficacy of the combined use as compared with the single use.

The present herbicide is especially valuable for the pre-emergence treatment of upland fields and for the early stage or middle stage control of weeds in paddy fields. The present invention embraces also the combined use with other herbicides in order to enlarge the range of controllable weed species or the range of time in which weeds are effectively controlled or to reduce the dosage of the present compound. For such purposes mention may be made of the combined use with, for example, one or more of phenoxy fatty acid herbicides such as, for example, 2,4-PA's (for example, ethyl 2,4-dichlorophenoxyacetate), MCP's (for example, ethyl 2-methyl-4-chlorophenoxyacetate, sodium 2-methyl-4-chlorophenoxyacetate and allyl 2-methyl-4-chlorophenoxyacetate) and MCPB (ethyl 2-methyl-4-chlorophenoxybutyrate); diphenyl ether herbicides such as, for example, NIP (2,4-dichlorophenyl 4'-nitrophenyl ether), CNP (2,4,6-trichlorophenyl 4'-nitrophenyl ether) and chlomethoxynil (2,4-dichlorophenyl 3'-methoxy-4'-nitrophenyl ether); s-triazine herbicides such as, for example, CAT [2-chloro-4,6-bis(ethylamino)-s-triazine], Prometryne [2-methylthio-4,6-bis(isopropylamino)-s-triazine] and Simetryne [2-methylthio-4,6-bis(ethylamino)-s-triazine]; carbamate herbicides such as, for example, molinate (S-ethylhexahydro-1H-azepin-1-carbothioate), MCC [methyl N-(3,4-dichlorophenyl)carbamate], IPC [isopropyl N-(3-chlorophenyl)carbamate] and Benthiocarb [S-(4-chlorobenzyl) N,N-diethylthiocarbamate]; and others such as DCPA (3,4-dichloropropionanilide), butachlor [2-chloro-2',6'-diethyl-N-(butoxymethyl)-acetanilide], alachlor [2-chloro-2',6'-diethyl-N-(methoxymethyl)acetanilide], and bentazon [3-isopropyl-2,1,3-benzothiadiazinone-(4)-2,2-dioxide]. The above abbreviations conform to the description in "Pesticide Manual, 1976" published by Japan Plant Protection Association.

The following examples illustrate this invention but are not intended to limit it in any way.

EXAMPLE 1

Synthesis of N-(p-trifluoromethoxyphenyl)-3,4,5,6-tetrahydrophthalimide 1.6 Grams (0.01 mole) of 3,4,5,6-tetrahydrophthalic anhydride and 1.8 g (0.01 mole) of p-trifluoromethoxyaniline were heated for two hours under reflux in 25 ml of glacial acetic acid. After having been cooled, the reaction mixture was poured into cold water and the precipitated crystals were collected by filtration, dried, and recrystallized from an ether-hexane mixture to obtain 2.4 g of the intended compound (melting point, 117°–118.5° C; 77% yield).

In a manner similar to above, 1.6 g (0.01 mole) of 3,4,5,6-tetrahydrophthalic anhydride and 2.0 g (0.01 mole) of p-trifluoromethylthioaniline were treated to obtain 2.3 g of N-(p-trifluoromethylthiophenyl)-3,4,5,6-tetrahydrophthalimide (melting point, 112°–114° C.; 70% yield).

In the following Examples all parts are by weight.

EXAMPLE 2

Wettable powder

| | Parts |
|---|---|
| Compound (1) | 50 |
| Clay-white carbon mixture containing major proportion of clay | 45 |
| Polyoxyethylene nonylphenyl ether | 5 |

The above ingredients were uniformly mixed and ground to prepare a wettable powder.

Example 3

Granule

| | Parts |
|---|---|
| Compound (2) | 5 |
| Bentonite-clay mixture | 90 |
| Calcium ligninsulfonate | 5 |

The above ingredients were uniformly mixed and ground. The mixture was kneaded together with a suitable amount of water and granulated to obtain a granule preparation.

EXAMPLE 4

Emulsifiable concentrate

| | Parts |
|---|---|
| Compound (1) | 20 |
| Xylene | 70 |
| Mixture of polyoxyethylene nonylphenyl ether and calcium alkylbenzenesulfonate | 10 |

The above ingredients were uniformly mixed to prepare an emulsifiable concentrate.

TEST EXAMPLE 1

A number of 1/10,000-are pots were filled with soil to simulate a paddy field and grown with injurious weeds of the leaf stage (plant ages in leaf number) shown below. Besides, young rice seedlings of the 2.5 leaf age were transplanted into the pot on the day before the chemical treatment (the chemical used was the emulsifiable concentrate of Example 4 extended with water). After 21 days, the percent control of growth relative to the untreated plot was estimated to obtain the results as shown in Table 1.

Weed species under test and their leaf stage:

| | Leaf stage |
|---|---|
| Barnyard grass | 1 |
| Monochoria | 2–3 |
| Umbrella plant | 2–3 |
| Slender spikerush | Early stage of multiplication |
| Arrowhead | 3 |

Evaluation:

(1) Herbicidal activity:

| | Percent growth control relative to untreated plot (%) |
|---|---|
| 5 | 100 |
| 4 | 90–99 |
| 3 | 80–89 |
| 2 | 60–79 |
| 1 | <60 |

(2) Chemical injury:

| | |
|---|---|
| H | High (including withering) |
| M | Medium |
| L | Low |
| N | None |

Table 1

| Compound No. | Dosage of active ingredient (g/are) | Rice | Barnyard grass | Monochoria | Umbrella plant | Slender spikerush | Arrowhead |
|---|---|---|---|---|---|---|---|
| 1 | 25 | L | 5 | 4 | 5 | 4 | 3 |
| | 12.5 | N | 5 | 3 | 5 | 3 | 2 |
| 2 | 25 | L | 5 | 4 | 5 | 4 | 3 |
| | 12.5 | N | 5 | 3 | 4 | 3 | 2 |
| A | 25 | N | 3 | 3 | 5 | 1 | 1 |
| | 12.5 | N | 2 | 2 | 3 | 1 | 1 |

Note:—
A = N-(p-chlorophenyl)-3,4,5,6-tetrahydrophthalimide [Agr. Biol. Chem., 40(4), 745-751 (1976)]

TEST EXAMPLE 2

A 1/10,000-are pot was filled with soil to simulate a paddy field and grown with a weed such as barnyard grass, monochoria, umbrella plant, hotarui or arrowhead to an early stage of growth and treated with a chemical under test. Thereafter, the procedure of Test Example 1 was followed to obtain the results as shown in Table 2.

Table 2

| Compound No. | Dosage of active ingredient (g/are) | Barnyard grass | Monochoria | Umbrella plant | Hotarui | Arrowhead |
|---|---|---|---|---|---|---|
| 1 | 25 | 5 | 5 | 5 | 4 | 3 |
| | 12.5 | 5 | 5 | 5 | 3 | 2 |
| A | 25 | 5 | 5 | 5 | 3 | 2 |
| | 12.5 | 5 | 5 | 5 | 2 | 1 |

TEST EXAMPLE 3

A polyethylene vat, 10 cm×20 cm×5 cm (depth), was filled with soil and seeded in drills with rice, barnyard grass, large crabgrass or redroot pigweed and covered with soil to a thickness of 1 cm. Prior to the emergence, the soil in the vat was treated in the same manner as in Test Example 1. Thereafter, the procedure of Test Example 1 was followed to obtain the results as shown in Table 3.

Table 3

| Compound No. | Dosage of active ingredient (g/are) | Growth control activity against | | |
|---|---|---|---|---|
| | | Rice | Barnyard grass | Large crabgrass | Redroot pigweed |
| 1 | 25 | L | 5 | 5 | 5 |
| | 12.5 | L | 5 | 5 | 5 |
| NIP (Control) | 25 | L | 5 | 5 | 4 |
| | 12.5 | L | 3 | 5 | 3 |

What is claimed is:
1. N-(p-trifluoromethoxyphenyl)-3,4,5,6-tetrahydrophthalimide.
2. A herbicidal composition comprising a carrier and as the active ingredient a herbicidally effective amount of N-(p-trifluoromethoxyphenyl)-3,4,5,6-tetrahydrophthalimide.
3. A process of controlling undesired plants comprising applying to the plants a herbicidally effective amount of the compound according to claim 1.
4. A process according to claim 3 wherein the undesired plants are weeds in a rice field and the amount of herbicide is insufficient to injure the rice.

* * * * *